（12） United States Patent
Wu et al.

(10) Patent No.: US 9,654,951 B2
(45) Date of Patent: May 16, 2017

(54) AUTOMATIC DISTRESS ALARMING METHOD AND ITS SYSTEM

(75) Inventors: Lai Ming Wu, Hong Kong (CN); Chui Ha Kung, Hong Kong (CN); Michael Tong Chang, Hong Kong (CN); Ka Ho Cheung, Hong Kong (CN); Heung Kai Chan, Hong Kong (CN); Choi Lam Cheung, Hong Kong (CN); Hon Wai Chan, Hong Kong (CN)

(73) Assignee: Lai Ming Wu, Hong Kong (CN)

( * ) Notice: Subject to any disclaimer, the term of this patent is extended or adjusted under 35 U.S.C. 154(b) by 28 days.

(21) Appl. No.: 13/461,786

(22) Filed: May 2, 2012

(65) Prior Publication Data

US 2017/0013431 A1 Jan. 12, 2017

(30) Foreign Application Priority Data

Feb. 24, 2012 (CN) .......................... 2012 1 0043065

(51) Int. Cl.
*H04M 11/04* (2006.01)
*H04W 4/22* (2009.01)
*G08B 25/01* (2006.01)
*H04M 1/725* (2006.01)
*G08B 21/04* (2006.01)
*A61B 5/117* (2016.01)

(52) U.S. Cl.
CPC ............ *H04W 4/22* (2013.01); *G08B 25/016* (2013.01); *A61B 5/117* (2013.01); *G08B 21/04* (2013.01); *G08B 21/043* (2013.01); *G08B 21/0446* (2013.01); *G08B 25/01* (2013.01); *H04M 1/72536* (2013.01)

(58) Field of Classification Search
CPC ....... H04W 4/22; G08B 25/016; G08B 25/01; G08B 21/04; G08B 21/043; G08B 21/0446; H04M 1/72536; A61B 5/117
See application file for complete search history.

(56) References Cited

U.S. PATENT DOCUMENTS

2002/0143489 A1* 10/2002 Orchard .................. G01P 13/00
702/141
2004/0199056 A1* 10/2004 Husemann ............ A61B 5/0002
600/300

FOREIGN PATENT DOCUMENTS

CN 101661661 A * 3/2010 ........... G08B 21/043

OTHER PUBLICATIONS

Google translation of: NC101661661A, "Automatic rescue alarm method and system", published Mar. 3, 2010, pp. 1-4 and Figure 1, Chen et al.*

* cited by examiner

Primary Examiner — Barry Taylor

(57) ABSTRACT

An automatic distress alarming method includes that: A. a distress alarm automatically sends out a sound and light alarming signal; B. the distress alarm automatically sends a distress signal and a GPS signal to a mobile phone; C. the distress alarm sends out the distress signal and the GPS signal by a manual operation; D. a disconnected distress alarm sends out the distress signal and the GPS signal. And its system includes a microprocessor U1, a driving chip U2, a wireless transmitting module U3, a switching circuit of an angular rate sensor, a GPS circuit, a storage device, a reset button, a manual operation alarming switch, a manual operation communicating switch and a disconnecting alarming button.

7 Claims, 7 Drawing Sheets

AUTOMATIC DISTRESS ALARMING METHOD AND ITS SYSTEM

CROSS REFERENCE OF RELATED APPLICATION

The present application claims priority under 35 U.S.C. 119(a-d) to CN 201210043065.5, filed Feb. 24, 2012.

BACKGROUND OF THE PRESENT INVENTION

Field of Invention

The present invention relates to an automatic distress alarming method using an angular rate sensor switching circuit and its system.

Description of Related Arts

At present, distress devices suitable for the olds, patients or disabled, or in dangerous site, such as fire rescue or military exercises, are gradually getting attention.

Chinese patents of publication numbers CN2143390Y, CN2108964U and CN201233643Y are provided. The patent of application number CN2143390Y discloses an automatic medical treatment alarming method as follows. When a patient is falling down after a sickness attack, a falling switch of a carry-on distress signal transmitter is turned on. And the distress signal transmitter sends a distress signal to an automatic distress alarming phone and starts the automatic distress alarming phone. According to the pre-stored phone numbers, the automatic distress alarming phone automatically dials phone numbers of a hospital or relatives and sends out a distress signal. The distress signal can be sent manually as well.

Patent of publication number CN2108964U has a basic function similar with the patent technique mentioned above.

Patent of publication number CN201233643Y relates to a fixed device which is used only for earthquake alarming, and can not meet the requirements of automatic distress alarming.

The techniques mentioned above generally uses a mercury switch as a trigger switch, which is easy to cause false operation or no operation at all. In addition, owing to the lack of global positioning system (GPS) positioning function, the techniques are not applicable to rescues outdoors or in the field.

SUMMARY OF THE PRESENT INVENTION

An object of the present invention is to provide an automatic distress alarming method and its system, which comprises a distress alarm that is capable of sending a distress signal and a GPS signal, and a mobile phone that receives the distress signal and the GPS signal and automatically dials for help. The distress alarm and the mobile phone are separated from each other, and communicate by wireless. The distress alarm and the mobile phone can be used independently. The distress alarm can be independent as a carry-on and automatically sensing device which is capable of automatically sending out a sound and light alarming signal for rescue, when a person's body is in a danger condition. Cooperated with wireless communication technique, the distress alarm extends the alarming signal for rescue to an infinite regional by common mobile phones. In case of a sudden loss of balance, the distress alarm generates an angular rate via a switching circuit of an angular rate sensor thereof. And the switching circuit of the angular rate sensor is triggered by the angular rate, and the distress alarm sends the distress signal and the GPS signal to the mobile phone. After receiving the distress signal, the mobile phone automatically dials rescue numbers for help. The automatic distress alarming method and its system are suitable for the olds, patients or disabled, or in dangerous site, such as fire rescue or military exercises.

A method to implement the present invention is as follows. The distress alarm can be independent as a carry-on and automatically sensing device which is able to automatically send out the sound and light alarming signal for rescue, when a person's body is in a danger condition. Meanwhile, the distress alarm is capable of sending the distress signal to the mobile phone which dials phone numbers and sends out the distress signal thereafter.

A. A method for the distress alarm automatically to send out the sound and light alarming signal, comprises:

connecting a micro controller unit (MCU) circuit of a microprocessor by a switching circuit of the angular rate sensor, when the distress alarm loses balance to a certain speed, wherein the micro controller unit (MCU) circuit starts timing, a light emitting diode (LED) circuit drives an LED light to flash, and after 10 seconds, a buzzer sounds and an alarming circuit turn s on an alarming light.

B. A method for the distress alarm automatically to send out the distress alarming signal and the GPS signal to the mobile phone comprises:

connecting a micro controller unit (MCU) circuit of a microprocessor by a switching circuit of the angular rate sensor, when the distress alarm loses balance to a certain speed, wherein the micro controller unit (MCU) circuit starts timing, a light emitting diode (LED) circuit drives an LED light to flash, and after 10 seconds, the buzzer sounds and an alarming circuit turns on an alarming light;

continually timing; wherein the MCU circuit extracts mobile phone numbers that receive the distress signal after 10 seconds; and drives a wireless transmitting circuit to send a distress signal to a mobile phone that receives the distress signal; at the same time, a GPS circuit sends informations of the alarming position through a wireless transmitting circuit to the mobile phone that receives the distress signal; and automatically dialing pre-stored phone numbers to seek for rescue, after receiving the distress signal and the GPS signal, by the mobile phone;

C. A method for the distress alarm to send the distress signal and the GPS signal comprises:

pressing a manual operation alarming button of the distress alarm, wherein a buzzer sounds immediately, simultaneously, the alarming light flashes and sends the distress alarming signal and the GPS signal to the mobile phone that receives the distress signal;

automatically dialing the pre-stored phone numbers to seek for rescue, after the mobile phone receiving the distress signal and the GPS signal;

D. A method for the distress alarm to send the distress signal and the GPS signal wirelessly comprises:

opening a normally closed switch under an external force in an unexpected situation; wherein the buzzer sounds immediately, simultaneously the alarming light flashes and automatically sends the distress signal and the GPS signal to the mobile phone that receives the distress signal.

automatically dialing the pre-stored phone numbers to seek for rescue, after the mobile phone for receiving the distress signal receives the distress signal and the GPS signal.

The method further comprises the following feature.

The mobile phone for receiving the distress signal is a common mobile phone with a normal conversation function, and includes the mobile phone of a help-seeker or others. The mobile phone has a wireless receiving module provided therein for receiving the distress signal and the GPS signal. When there is not the distress signal and the GPS signal, the mobile phone is a common and independently used mobile phone.

The method further comprises communicating with following steps:

pressing an inquiring button of the distress alarm which immediately sends out an inquiring signal to the mobile phone for receiving the distress signal;

automatically dialing numbers of a registered phone for communicating, when the mobile phone for receiving the distress signal receives the inquiring signal.

The method further comprises sense warning with the following steps:

starting a manual operation alarming immediately after a circuit switch of a sensing module is started by an outer connected sensing interface, wherein the buzzer sounds immediately, simultaneously the alarming light flashes and automatically sends out the distress signal and the GPS signal;

automatically dialing the pre-stored phone numbers to seek for rescue, after the mobile phone receives the distress signal and the GPS signal.

pressing a reset button to cancel the alarming within 10 seconds of the timing in case of a false triggering.

Systems to implement the present invention comprise a distress alarm which is capable of being independent as a carry-on, automatically sensing system which automatically sends out a sound and light alarming signal when a person's body is in a danger condition, and a system capable of sending a distress signal and a GPS signal to the mobile phone which dials numbers and sends out the distress signal thereafter, wherein the distress alarm comprises a microprocessor U1, a driving chip U2 and a wireless transmitting module U3, wherein a switching circuit of an angular rate sensor, a GPS circuit, a storage device, a reset button, a manual operation alarming switch, a manual operation communicating switch and a disconnecting alarming button are respectively connected to the driving chip U2 via the microprocessor U1, and the driving chip U2 is respectively connected with the wireless transmitting module U3, a light emitting diode (LED) and a buzzer; wherein the microprocessor MCU starts timing when the switching circuit of the angular rate sensor is turned on, and the LED light flashes at the same time, and after 10 seconds, the buzzer sounds and an alarming light is on simultaneously;

wherein the mobile phone has a wireless receiving module provided therein, wherein when the buzzer sounds and the alarming light is on simultaneously, timing is kept on, and after 10 seconds, the distress alarm automatically sends out the distress signal and the GPS signal to a specified mobile phone which automatically dials the pre-stored numbers to ask for rescue, after receiving the distress signal.

What the automatic distress alarming system further comprises is as follows.

The distress alarm comprises a concrete alarming circuit which comprises a microprocessor U1, a driving chip U2, a wireless transmitting module U3, a switching circuit of an angular rate sensor, a GPS circuit, a storage device, a reset button, a manual operation alarming switch, a manual operation communicating switch, a disconnecting alarming button, a light emitting diode (LED), a buzzer and a relay; wherein pins 4, 5, 6, 7, 8, 9, 10 and 40 of the microprocessor U1 are respectively connected with the switching circuit of the angular rate sensor, the GPS circuit, a balance switch, the manual operation alarming switch, the manual operation communicating switch, the disconnecting alarming button, the reset button and the storage device; pins 29, 30 and 31 of the microprocessor U1 are respectively connected with the buzzer, the light emitting diode (LED) and the relay via the driving chip U2; the wireless transmitting module U3 is connected with the relay; a resistor R1 is connected across a pin 10 of the microprocessor U1 and the ground.

The present invention has beneficial effects as follows. The automatic distress alarming system has no region and scope limitation. The distress alarm and the mobile phone are separated devices and communicate by wireless communication. The distress alarm and the mobile phone can be used independently. The distress alarm can be independent as a carry-on and automatically sensing device which is capable of automatically sending out the sound and light alarming signal for rescue, when a person's body is in a danger condition. Cooperated with wireless communication technique, the distress alarm extends the alarming signal for rescue to an infinite regional by the commonly used mobile phone. The distress alarm is capable of sending the distress signal and the GPS signal at the same time, improves the rescue efficiency, saves the rescue time, and is especially suitable for field usage.

The distress alarm has functions of automatic and manual alarming for rescue. In a standby mode, the mobile phone is a completely independent mobile phone which is capable of calling in and out. The distress alarm has a built-in timing device which is capable of automatically triggering the timing of a correct alarming dial. And if the triggering is judged to be false, the timing device is capable of automatically or manually resetting. If the alarming signal is triggered 10 seconds before locking and transmitting the alarming signal, the timing device returns to a normal position, which is capable of cancelling the alarming action without the manual operation, and achieving a function of a fully automated alarming cancel. In addition, the distress alarm has a simple structure and is convenient to carry and use.

These and other objectives, features, and advantages of the present invention will become apparent from the following detailed description, the accompanying drawings, and the appended claims.

DETAILED DESCRIPTION OF THE PREFERRED EMBODIMENT

Figure 1:
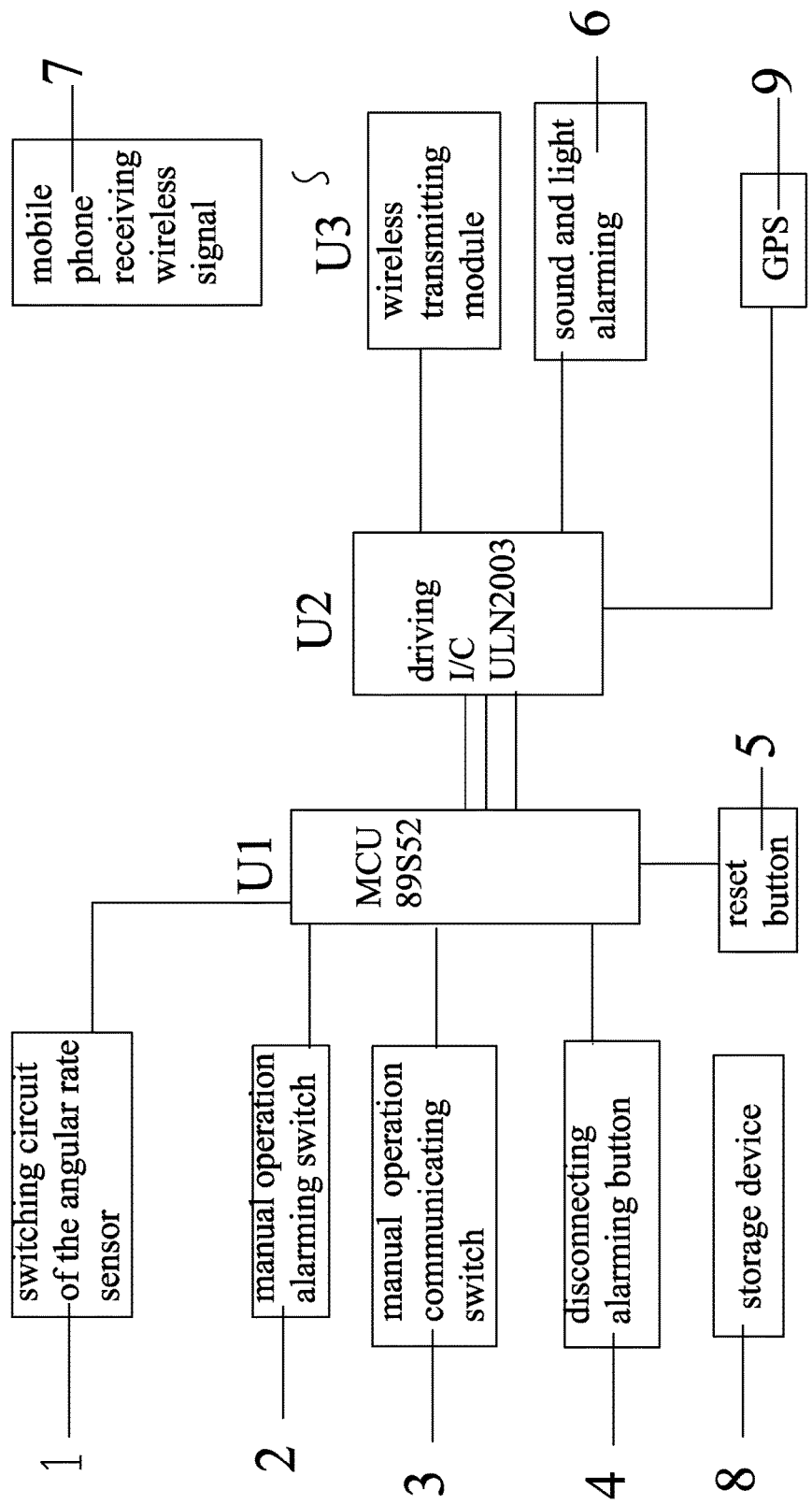
FIG. 1 is a block diagram of a system according to the present invention.
Figure 2:
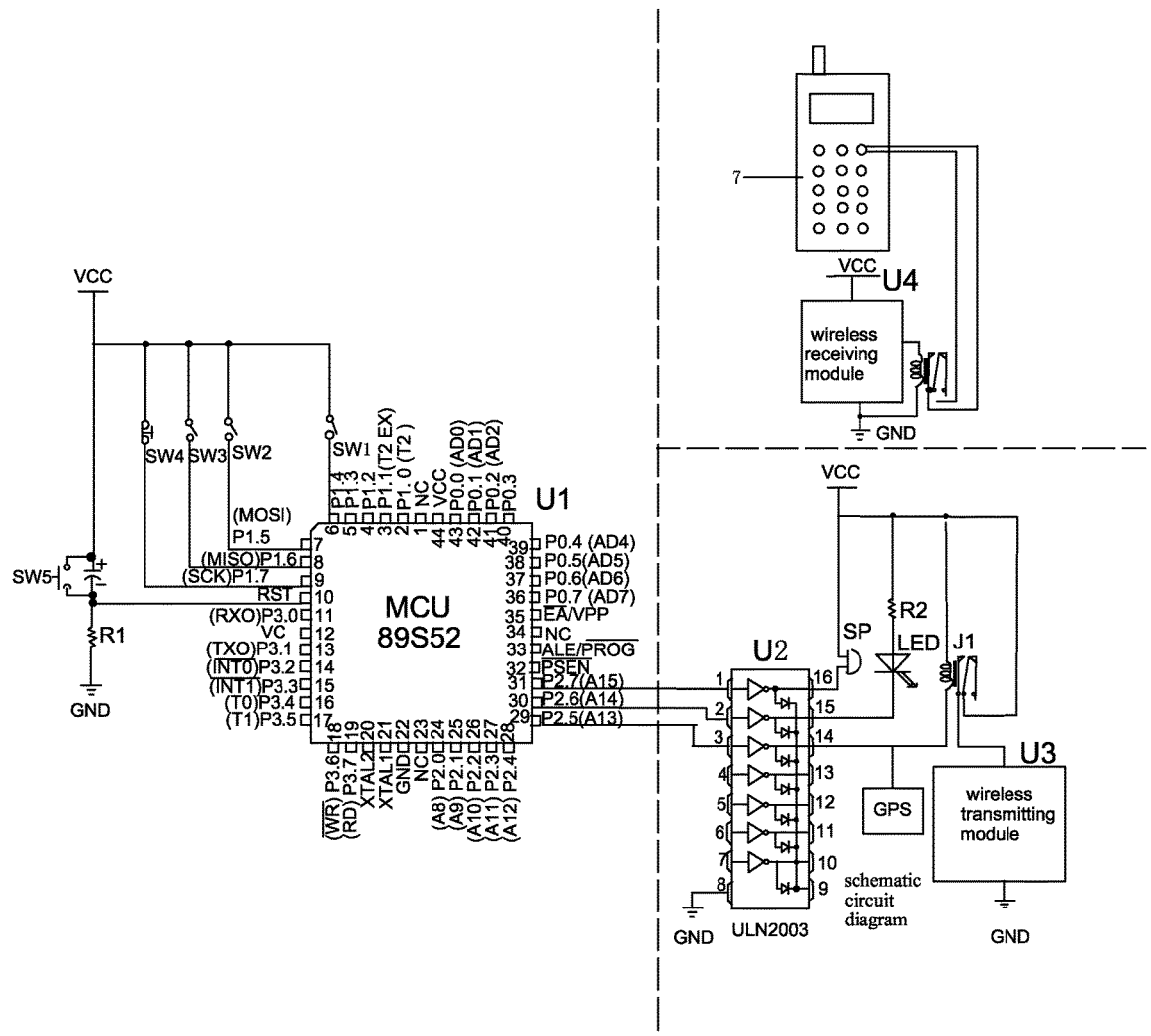
FIG. 2 is a schematic circuit diagram of FIG. 1.
Figure 2A:
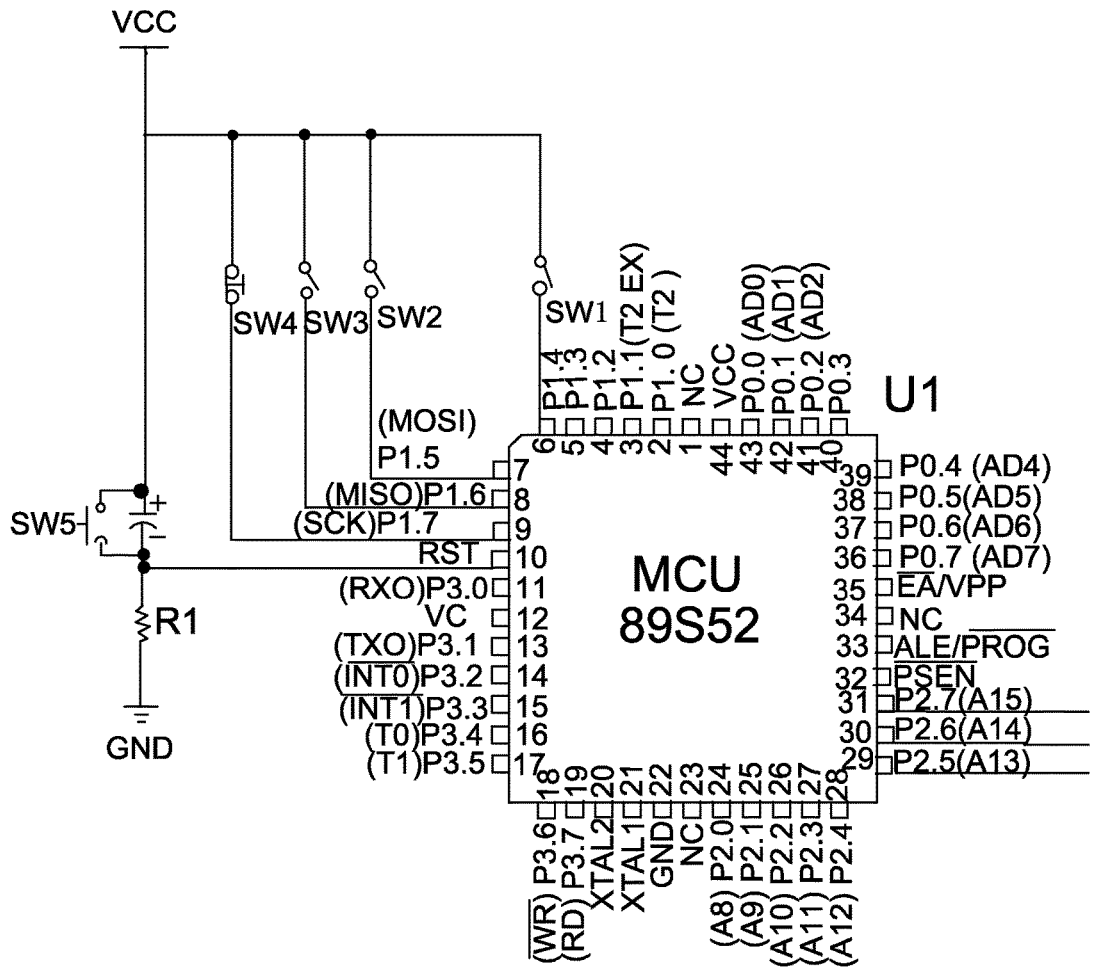
FIG. 2A is an enlarged view of a first part of the FIG. 2.
Figure 2B:
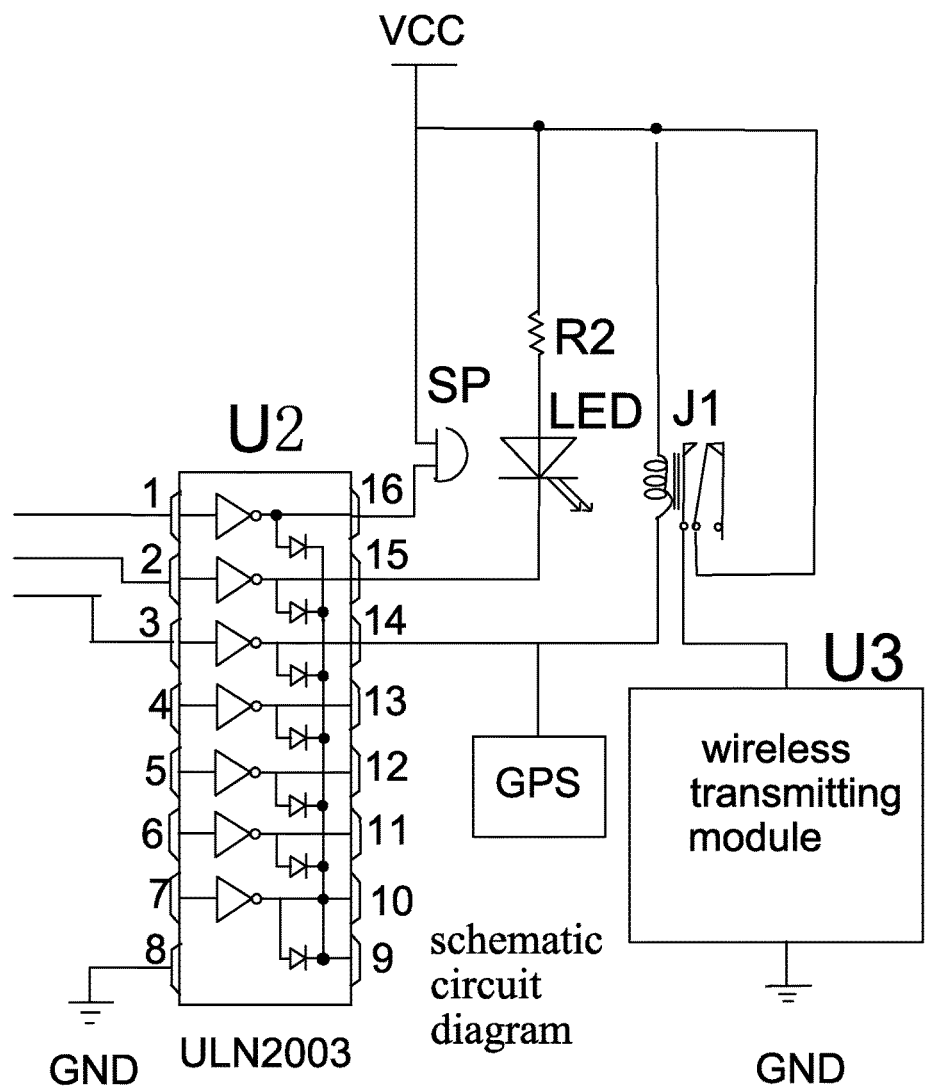
FIG. 2B is an enlarged view of a second part of the FIG. 2.
Figure 2C:
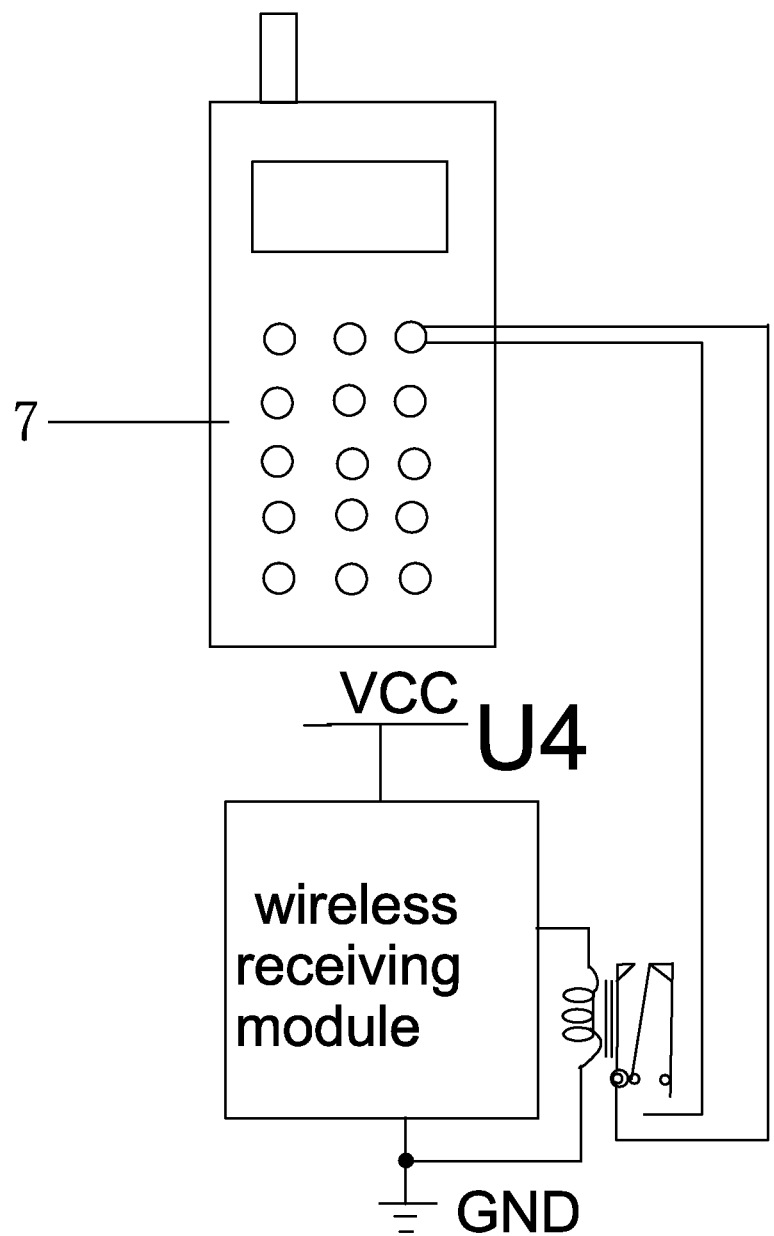
FIG. 2C is an enlarged view of a third part of the FIG. 2.
Figure 3A:
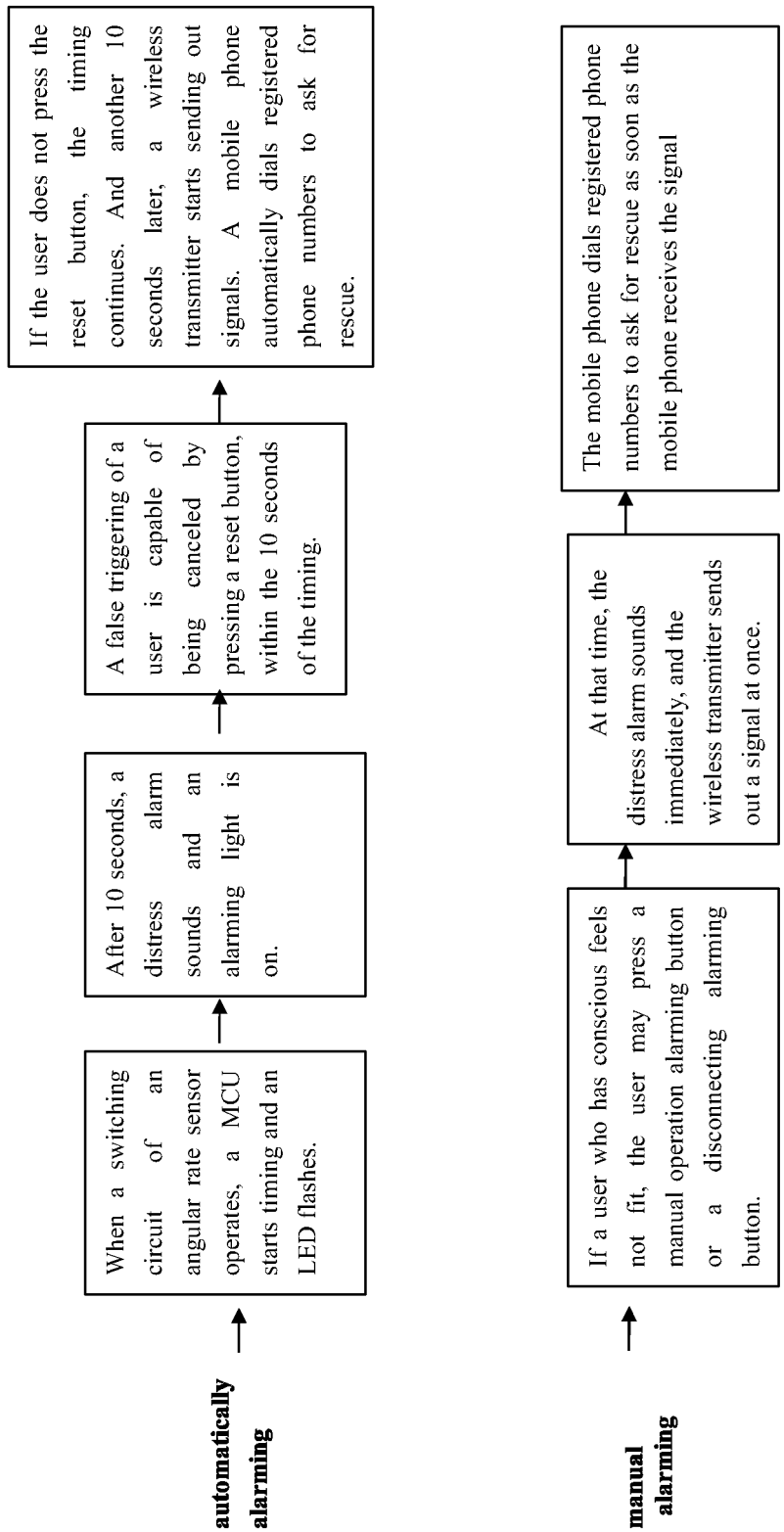
FIG. 3 is a flow diagram of an alarming method according to the present invention.
Figure 3B:
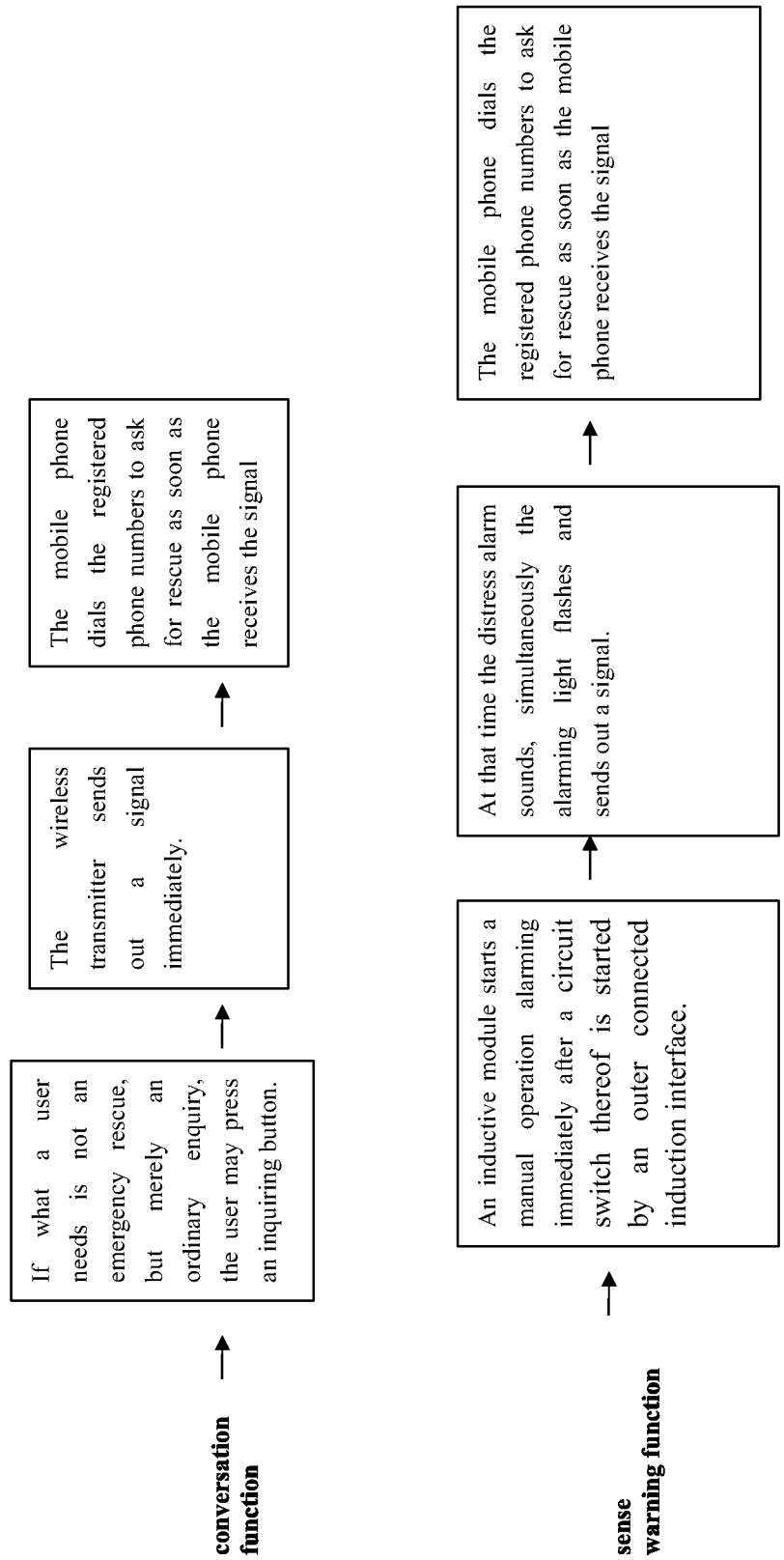

Further description is illustrated combining with attached drawings and preferred embodiments according to the present invention.

As shown in the drawings attached, the present distress alarming system consists of a distress alarm, a mobile phone 7 and a network, wherein the distress alarm comprises a switching circuit 1 of an angular rate sensor, a manual operation alarming switch 2, a manual operation communicating switch 3, a disconnecting alarming button 4, a reset button 5, a sound and light alarming device 6, a microprocessor U1, a driving chip U2 and a wireless transmitting module U3, a storage device 8 and a GPS circuit 9, wherein the mobile phone 7 has a wireless receiving module U4 provided therein.

Preferred Embodiment 1: (See the Drawings Attached)

Take an old man wearing the distress alarm as an example. When the man falls down and gets hurt carelessly at home, or gets ill and is not able to move, the switching circuit of the angular rate sensor is connected. At this moment, after receiving the distress signal, the wireless transmitting module in the distress alarm automatically sends out a distress signal and a GPS signal to a help-seeking mobile phone which automatically dials pre-stored numbers, such as a nearest neighbor, so as to get a timely rescue.

If the disconnecting switch is connected by a false operation, the distress alarming procedure can be cancelled in an effective time by the reset button provided thereon.

Functions and usages of the present are as follows.

The present distress alarming system is suitable for any network covering wireless phone, without a specific system, and is suitable for any mode of wireless phone existed.

The alarm of the present distress alarming system can be used as an independent distress alarm.

The modules of the present invention distress alarming system can be installed in the mobile phone to serve as an integrated distress alarming mobile phone manually and automatically.

The present distress alarming system is suitable for anyone with a requirement, and especially the olds, disabled, hikers and latecomers.

The module of the present invention distress alarming system can be installed in a device which needs a fall-off alarming rescue, such as a baby carriage or an electric wheelchair.

The module of the present invention distress alarming system can be installed in a device which needs sense warning, such as a safety and security facility, a dam and an exemption slope.

Features of the present invention are as follows.

1. The automatic distress alarm is a device that is capable of automatically alarming and dialing for help by a mobile phone.

2. The mobile phone is capable of being used independently offline as a common mobile phone. Ordinarily, the mobile phone is capable of calling in and out and being regarded as an independent mobile phone.

3. The distress alarm comprises: a. a switching circuit of an angular rate sensor; b. a manual operation alarming switch for connecting buttons; c. a manual operation communicating switch for connecting buttons and driving a transmitter to send out the alarming signal; d. a disconnecting alarming switch for functioning when the switch is disconnected, wherein the switch is usually closed, and opens under external force in unexpected situation, at that time, the buzzer sounds immediately, the alarming light is on simultaneously, and the distress alarm sends the distress signal and the GPS signal to a specified mobile phone, wherein the distress alarm is suitable for collapse of a dam, collapse or cracking of a building, landslide of a mountain, as well as security of windows and doors; e. a reset button for connecting elastic switch; and f. a mobile phone, provided a corresponding channel receiver therein, which starts a swift dialing function of the mobile phone and automatically dials phone numbers of a neighbor, relative or first-aid station.

The automatically dialing function is accomplished by a set of wireless receiving module and a built-in relay.

Principles of the automatically dialing are as follows. After receiving a signal transmitted by the transmitting module, the wireless receiving module outputs a +ve voltage to the relay. Accordingly, the relay is electrified, a contacting switch closes which triggers a function of "automatically dialing by one button" of the mobile phone. And the mobile phone automatically dials the pre-stored numbers of an aiming person or organization to seek for help.

The main concepts of the present system are carry-on, automatically detecting individual physical state in critical condition, then triggering the alarming device. The present system firstly asks someone around for help, then triggers a transmitting signal to an equipment which has receiving device, such as the mobile phone, so as to dial the pre-stored phone numbers asking for help. It is worth mentioning that the mobile phone refers not only to a mobile phone, but also any device that has a corresponding receiving equipment provided therein. What the present invention emphasizes is a system of carry-on, automatically detecting and then triggering the alarming And conventionally disclosed techniques all have no ideas of "carry-on, automatically detecting".

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. An automatic distress alarming method comprises providing a distress alarm which is capable of automatically sending out a sound and light alarming signal for rescue when a person's body is in a danger condition, wherein the distress alarm is capable of sending a distress signal to a mobile phone which dials phone numbers and sends out the distress signal thereafter, A: wherein a method for the distress alarm automatically to send out the sound and light alarming signal comprises:

connecting a micro controller unit (MCU) circuit of a microprocessor by a switching circuit of the angular rate sensor, when the distress alarm loses balance to a certain speed, wherein the micro controller unit (MCU) circuit starts timing; a light emitting diode (LED) circuit drives an LED light to flash, and after 10 seconds, the buzzer sounds and an alarming circuit turns on an alarming light;

B: wherein a method for the distress alarm automatically to send out the distress alarming signal and a GPS signal to the mobile phone comprises:

connecting a micro controller unit (MCU) circuit of a microprocessor by a switching circuit of the angular rate sensor, when the distress alarm loses balance to a certain speed, wherein the micro controller unit (MCU) circuit starts the step of timing, a light emitting diode (LED) circuit drives an LED light to flash, and after 10 seconds, the buzzer sounds and the alarming circuit turns on the alarming light, continually timing, wherein the MCU circuit extracts mobile phone numbers that receive the distress signal after 10 seconds; and drives a wireless transmitting circuit to send a distress signal to a mobile phone that receives the distress signal; at the same time, a GPS circuit sends informations of the alarming position through a wireless transmitting circuit to the mobile phone that receives the distress signal; and automatically dialing pre-stored phone numbers to seek for rescue, after receiving the distress signal and the GPS signal, by the mobile phone;

C: wherein a method for the distress alarm to send the distress signal and the GPS signal comprises:

pressing a manual operation alarming button of the distress alarm; wherein a buzzer sounds immediately; simultaneously the alarming light flashes and sends the distress alarming signal and the GPS signal to the mobile phone that receives the distress signal; and automatically dialing the pre-stored phone numbers to seek for rescue, after the mobile phone receiving the distress signal and the GPS signal; and D: wherein a method for the distress alarm to send the distress signal and the GPS signal wirelessly comprises:

opening a normally closed switch under an external force in an unexpected situation; wherein the buzzer sounds immediately; simultaneously the alarming light flashes and automatically sends the distress signal and the GPS signal to the mobile phone that receives the distress signal; and, automatically dialing the pre-stored phone numbers to seek for rescue, after the mobile phone for receiving the distress signal receives the distress signal and the GPS signal.

2. The automatic distress alarming method, as recited in claim 1, wherein the mobile phone for receiving the distress signal is a common mobile phone with a normal conversation function, and comprises the mobile phone of a help-seeker or others, wherein the mobile phone has a wireless receiving module provided therein for receiving the distress signal and the GPS signal, wherein when there is not the distress signal and the GPS signal, the mobile phone is a common and independently used mobile phone.

3. The automatic distress alarming method, as recited in claim 1, wherein the method further comprises communicating with following steps of:

pressing an inquiring button of the distress alarm which immediately sends out an inquiring signal to the mobile phone for receiving the distress signal;

automatically dialing numbers of a registered phone for communicating, when the mobile phone for receiving the distress signal receives the inquiring signal.

4. The automatic distress alarming method, as recited in claim 1, wherein the method further comprises an sense warning with following steps of:

starting a manual operation alarming immediately after a circuit switch of a sensing module is started by an outer connected sensing interface; wherein the buzzer sounds immediately, simultaneously the alarming light flashes and automatically sends out the distress signal and the GPS signal;

automatically dialing the pre-stored phone numbers to seek for rescue, after the mobile phone receives the distress signal and the GPS signal.

5. The automatic distress alarming method, as recited in claim 1, further comprises pressing a reset button to cancel the alarming method within 10 seconds of timing in case of a false triggering.

6. An automatic distress alarming system to implement the automatic distress alarming method, as recited in claim 1, comprising a distress alarm which is capable of being independent as a carry-on, automatically sensing system which automatically sends out a sound and light alarming signal when a person's body is in a danger condition, and a system capable of sending a distress signal and a GPS signal to the mobile phone which dials numbers and sends out the distress signal thereafter;

wherein the distress alarm comprises a microprocessor U1, a driving chip U2 and a wireless transmitting module U3, wherein a switching circuit of an angular rate sensor, a GPS circuit, a storage device, a reset button, a manual operation alarming switch, a manual operation communicating switch and a disconnecting alarming button are respectively connected to the driving chip U2 via the microprocessor U1, and the driving chip U2 is respectively connected with the wireless transmitting module U3, a light emitting diode (LED) and a buzzer; wherein the micro controller unit (MCU) starts timing when the switching circuit of the angular rate sensor is turned on, and the LED light flashes at the same time, and after 10 seconds, the buzzer sounds and an alarming light is on simultaneously;

wherein the mobile phone has a wireless receiving module provided therein, wherein when the buzzer sounds and the alarming light is on simultaneously, timing is kept on, and after 10 seconds, the distress alarm automatically sends out the distress signal and the GPS signal to a specified mobile phone which automatically dials the pre-stored numbers to ask for rescue, after receiving the distress signal.

7. The automatic distress alarming system, as recited in claim 6, wherein a particular alarming circuit which comprises the microprocessor U1, the driving chip U2, the wireless transmitting module U3, the switching circuit of the angular rate sensor, the GPS circuit, the storage device, the reset button, the manual operation alarming switch, the manual operation communicating switch, the disconnecting alarming button, the light emitting diode (LED), the buzzer and a relay; wherein pins (4), (5), (6), (7), (8), (9), (10) and (40) of the microprocessor U1 are respectively connected with the switching circuit of the angular rate sensor, the GPS circuit, a balance switch, the manual operation alarming switch, the manual operation communicating switch, the disconnecting alarming button, the reset button and the storage device; pins (29), (30) and (31) of the microprocessor U1 are respectively connected with the buzzer, the light emitting diode (LED) and the relay via the driving chip U2; the wireless transmitting module U3 is connected to the relay; a resistor R1 is connected across a pin (10) of the microprocessor U1 and the ground.

* * * * *